United States Patent [19]
Hack

[11] Patent Number: 6,096,942
[45] Date of Patent: Aug. 1, 2000

[54] SURGICAL DRESSING, AND PROCESS FOR MANUFACTURING SAME

[75] Inventor: Bradford H. Hack, Arcadia, Calif.

[73] Assignee: Pabban Development Inc., Costa Mesa, Calif.

[21] Appl. No.: 09/066,025

[22] Filed: Apr. 24, 1998

[51] Int. Cl.[7] .................................................. A61F 13/00
[52] U.S. Cl. ................................ 602/41; 602/48; 602/56
[58] Field of Search .............................. 602/41, 48, 56

[56] References Cited

U.S. PATENT DOCUMENTS 4,793,337  12/1988  Freeman et al .
5,010,883  4/1991  Rawlings et al. .
5,843,254  12/1998  Clark .

*Primary Examiner*—John G. Weiss
*Assistant Examiner*—Paul Shanoski
*Attorney, Agent, or Firm*—G. Donald Weber, Jr.

[57] ABSTRACT

An absorbent dressing which does not stick to the wound to thereby minimize secondary lesions which are caused by shearing stresses and the like. The dressing includes an absorbent pad and a thin support film with an adhesive layer therein to maintain the dressing in place on a patient. A backer sheet supports the film and a release liner covers the adhesive layer. The support film is, preferably, transparent or translucent which permits visual inspection of the pad.

15 Claims, 1 Drawing Sheet

SURGICAL DRESSING, AND PROCESS FOR MANUFACTURING SAME

BACKGROUND

1. Field of the Invention

The present invention relates to an absorbent surgical dressing, in general, and, more particularly, to a wound or surgical dressing comprising an absorbent pad, an envelope layer which does not stick to the wound surrounding the pad, and the adhesive film attached to the envelope/pad configuration and adapted to attach the envelope/pad combination to a patient adjacent to a wound site.

2. Prior Art

Absorbent surgical dressings are known in the art. Such dressings are frequently mounted on adhesive strips or sheets. These devices are frequently referred to as "band-aids" or the like and are sold by many suppliers under various trademarks and/or trade names. In these devices, wound secretions can be taken up by the absorbent pad which is attached to a patient by the adhesive strip. However, in the prior art, the absorbent dressing frequently sticks to the wound. Thus, secondary injuries are caused and wounds are reopened when a dressing is changed. As a result, healing is frequently delayed.

In certain known absorbent surgical dressings, the absorbent pad is arranged as an internal pad in an envelope layer but is connected to the envelope layer. Thus, if the part of the body covered with the dressing is moved or shifted, the absorbent pad moves the envelope layer with it. This results in shearing stresses on the envelope layer and, indirectly, on the wound surface. Again, this action can cause secondary injuries.

Moreover, in many of the prior art dressing devices, the absorbent pad is covered by an opaque covering whereby it is difficult (if not impossible) to observe the condition of the pad.

In other situations, for example, for larger wounds such as created by surgical procedures, the absorbent surgical dressing is quite large and there is no provision for adhering the dressing to the wound site. Thus, a separate adhesive strip or strips must be added to secure the pad in place. These strips may be awkward to apply. Also, the large dressing is difficult to apply in many cases. As a result, the absorbent dressing is frequently exposed to the ambient conditions which can lead to problems of "bleed-through" and/or exposure to dirt, germs or the like.

CO-PENDING APPLICATION

Reference is made to co-pending application entitled ABSORBENT SURGICAL DRESSING AND PROCESS FOR MANUFACTURING SAME by B. Hack et al bearing Ser. No. 08/796,266 and filed on Feb. 7, 1997, now abandoned.

PRIOR ART STATEMENT

Listed herewith are patents relating to dressing devices.

U.S. Pat. No. 5,512,041; WOUND DRESSING FOR PROMOTING MOIST WOUND HEALING; Bogart. This patent is directed to a wound dressing for promoting moist wound healing and comprising a backing sheet coated with a pressure sensitive adhesive, an absorbent pad adhered to the adhesive and a net extending across the pad and adhered to the adhesive.

U.S. Pat. No. 5,468,253; ELASTOMERIC MEDICAL DEVICE; R. S. Bezwada et al. This patent is directed to a medical device formed from bioabsorbable elastomers.

U.S. Pat. No. 5,409,472; ADHESIVE POLYMERIC FOAM DRESSINGS; D. A. Rawlings et al. This patent is directd to a conformable wound dressing which includes a polymeric foam absorbent layer, an adhesive layer and a layer of liquid impervious moisture vapor material.

U.S. Pat. No. 5,395,305; MULTI LAYER WOUND COVERING MATERIALS COMPRISING A SUPPORTING LAYER AND A MOISTURE PERMEATION CONTROLLING LAYER AND METHOD FOR THEIR MANUFACTURE; M. Koide et al. This patent is directed to wound covering materials comprising a support layer which is to be in contact with the wound and a moisture permeation controlling layer which may contain an antimicrobial agent.

U.S. Pat. No. 4,617,021; ABSORBENT SURGICAL DRESSING AND PROCESS FOR MANUFACTURING SAME; H. Leuprecht. This patent is directed to a surgical dressing which includes an absorbent pad loosely contained within an envelope formed of hydrophobic material.

U.S. Pat. No. 4,423,101; ABSORBENT PRODUCTS; D. A. Willstead. This patent is directed to absorbent products such as plasters, bandages or wound dressings or the like.

U.S. Pat. No. 4,105,033; POWDER GRAFTED CELLULOSE; P. K. Chatterjee et al. This patent is directed to a powdery form of a graft copolymer containing hydrophilic chains which provide a highly moisture absorbent medium.

U.S. Pat. No. 3,971,379; ABSORBENT HYDROPHILIC CELLULOSIC PRODUCT; P. K. Chatterjee. This patent is directed to an absorbent body used for products such as diapers, wound dressings, sanitary napkins and the like.

SUMMARY OF THE INSTANT INVENTION

This invention provides an absorbent wound dressing which does not stick to the wound to thereby minimize secondary lesions which can be caused by shearing stresses and the like when a patient wearing the dressing moves. The dressing includes an absorbent pad disposed within a flexible envelope layer. When bending movements by the patient occur and there are stresses from surface forces, the internal pad can move within the envelope layer. However, the envelope remains securely on the wound, free of shearing forces which would cause lateral shifting. This obviates secondary lesions to the wound. Although any suitable material which does not stick to the wound can be used to make the lattice structure of the envelope layer, polypropylene is a suitable material. which does not stick to the wound thereby enhancing the wound healing.

A thin, flaccid support layer with an adhesive surface is provided to adhere to the envelope layer of the absorbent dressing and to maintain the dressing in place on a patient. The support layer is transparent or translucent in order to permit visual inspection of the pad without handling the dressing.

A backer sheet is removably adhered to the non-adhesive surface of the support layer by adhesive and/or eletrostatic attraction. The backer sheet provides mechanical substance for the support layer until after the dressing has been placed upon the patient, at which time the backer sheet is, generally, unnecessary and may be removed, if so desired.

A release liner is removably adhered to the adhesive surface of the support layer. The release liner is removed prior to the application of the dressing to the wound site of the patient.

DESCRIPTION OF A PREFERRED EMBODIMENT

Figure 1:
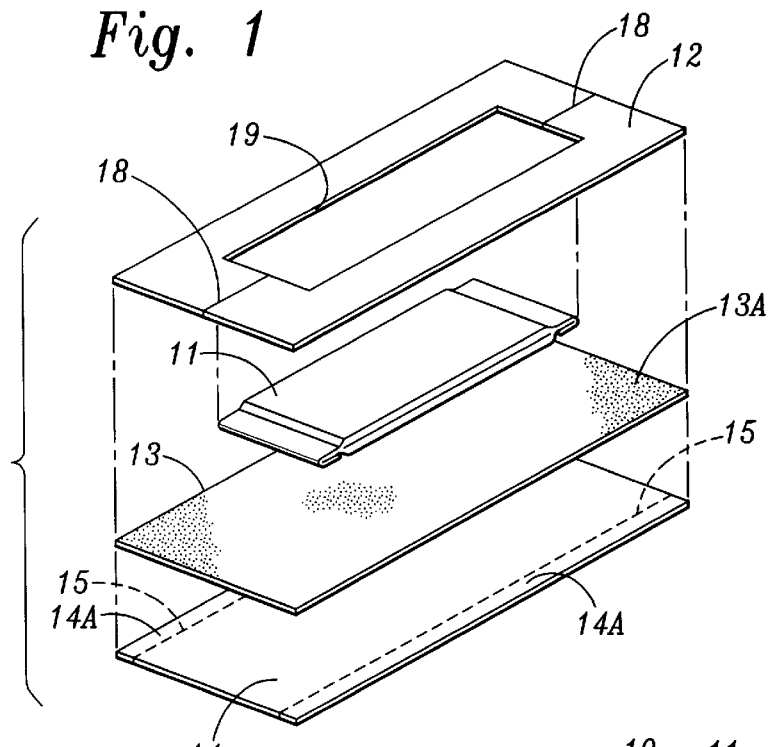
FIG. 1 is an exploded view of one embodiment of an absorbent surgical dressing according to the instant invention.

Referring now to FIG. 1, there is shown an exploded view of a surgical dressing 10 which represents one embodiment of the instant invention.

The dressing 10 includes an absorbent pad and envelope assembly 11, a release liner 12, a flexible, flaccid, adhesive surfaced support film 13 and a backer sheet 14.

The absorbent assembly pad 11 is, preferably, formed of a highly absorbent, disposable pad which is capable of absorbing and retaining aqueous fluids. The assembly pad 11 includes a cellulosic core and a non-woven polyester envelope or cover stock. The absorbent assembly pad 11 is described in greater detail hereinafter. This assembly is described in the abandoned application by B. Hack et al referenced supra. This description is included herein by reference thereto.

The release liner 12 is a typical release liner which is applied to the adhesive surface of the adhesive tape or membrane 13, but is readily removable therefrom. In typical cases, the release liner 12 can be fabricated of paper, gauze, plastic or the like. Many such materials are known in the art. One preferred material is 60# siliconized kraft release paper.

The relative dimensions of the release liner 12 are such that the release liner 12 engages the adhesive surface of the membrane 13 but does not engage or overlie the portion of the adhesive surface of membrane (or film) 13 which adheres to the pad assembly 11. The release liner 12 may include one or more slits 18 therein to facilitate removal of the release liner 12 when the dressing 10 is applied to a patient.

The flexible support film 13 is, typically, formed of a suitable thin material such as 0.75 polyurethane, for example. This film (or membrane) is, typically, impervious to fluid but is referred to as "breathable" and can be either transparent or translucent in order to permit visual inspection of the assembly pad 11.

The film includes an adhesive surface 13A which is, preferably, formed of a medical grade adhesive or surface which is of the HY-3 high MVTR type. The materials used for the film demonstrate, generally, strength, flexibility and an hydrophobic medium.

In a preferred embodiment, the backer sheet 14 includes appropriate slits 15 (shown in dashed lines) adjacent to the edges thereof. The slits 15 permit selective removal of the narrow edge portions 14A which facilitates removal of the backer sheet 14 when the dressing 10 is in place on the patient.

The support mechanism of the dressing (i.e. the dressing without the pad assembly 11) is, typically fabricated as a four-layered laminate comprising the backer sheet 14 (which may be a polyester casting sheet), the flaccid film or membrane 13 (which may be a matte finish polyurethane film), a medical grade, pressure sensitive adhesive layer (or surface) 13A on film 13 and a release liner 12. These layers are, typically, placed one upon the other to form a unitary strip of material.

The strip of material is then die cut in one or two steps in order to provide the slits 15 adjacent to at least one edge of the strip. Also, cuts are made in the liner 12 to form the opening 19 therethrough and to provide the slits 18 at suitable locations in the liner 12.

The pad assembly 11 is then placed in engagement with the adhesive surface 13A of film 13 which is not covered by the release liner 12, i.e. the portion of the adhesive surface exposed through the opening 19 in liner 12.

Thus, in the final product assembly 10, the release liner 12 and the absorbent pad assembly 11 are adhered to the adhesive surface 13A of membrane 13. The pad assembly 11 is substantially permanently adhered to film 13 while the release liner 12 is, of course, selectively removable. When the release liner 12 is removed from the adhesive surface 13A of the assembled dressing 10, the dressing is placed over the wound such that the absorbent pad assembly 11 is adjacent to the wound. The adhesive surface 13A of film or membrane 13 is used to adhere the pad 11 to the patient adjacent to the wound.

When the dressing 10 is in place, the backer 14, which is rather stiff compared to the flaccid film 13, is removed from the dressing 10. The thin flaccid film 13 readily and easily conforms to the wound site and to the pad assembly 11. Moreover, the film is quite lightweight and flexible so that it is comfortable to the user.

In the preferred embodiment, a visual inspection of the absorbent pad 11 is readily obtained because of the translucent or transparent characteristic of the membrane 13. However, because the film 13 is impervious, fluids, medications, effluvia or the like are unable to pass through the film 13 and are retained in the absorbent pad assembly 11. As noted, the absorbent pad assembly 11 is highly absorbent and retains the aforementioned fluid materials.

Figure 2:
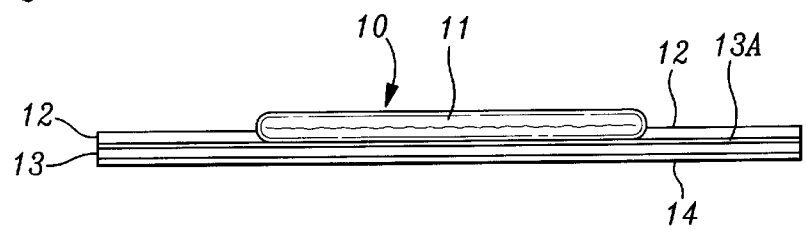
FIG. 2 is a partially broken away elevation view of the instant invention taken at about the longitudinal midpoint of an assembled embodiment thereof.

Referring now to FIG. 2, there is shown a partially broken away elevation view taken at about the lengthwise midpoint of an assembled embodiment of the invention as shown in FIG. 1. This view shows the dressing 10 fully assembled. It is seen that the backer 14 is the basic support component for the dressing 10. The membrane 13 is adhered to the major surface of the backer sheet 14, for example by low tack adhesive or electrostatic attraction. The adhesive surface 13A of tape or film 13 is adhered to the absorbent pad assembly 11 or to the release liner 12, as described supra. In particular, the pad assembly 11 is adhered to the adhesive surface 13A at the center of membrane 13 where the opening 19 is formed in liner 12.

It is seen that in use, the release liner 12 is removed and the dressing is applied to the wound site with the pad assembly 11 adjacent to the wound. The adhesive surface 13A of membrane 13 adheres to the patient. The backer sheet 14 is then removed whereupon the flaccid membrane 13 conforms to the pad 11 and the patient's body.

Figure 3:
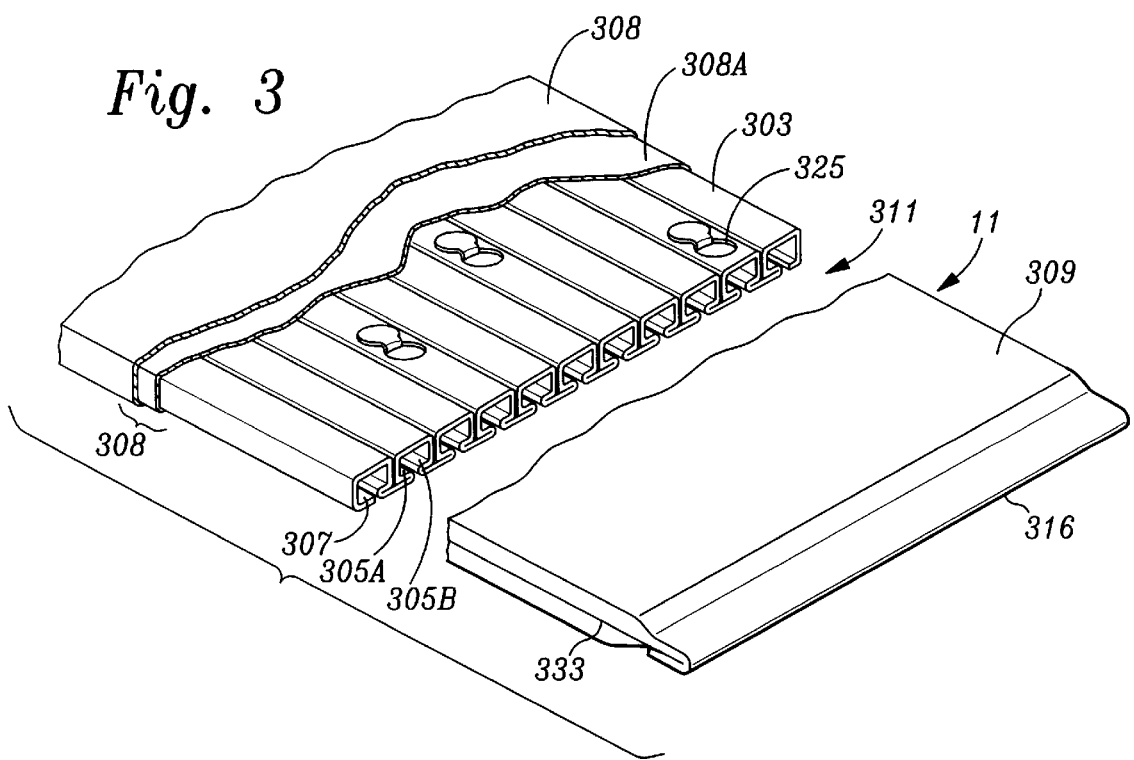
FIG. 3 is a detailed partially broken away view of one embodiment of the absorbent pad of the instant invention.

Referring now to FIG. 3, there is shown a partially broken away, partially cross-sectional view of the pad 11 used in a preferred embodiment of the instant invention.

In a preferred embodiment, the absorbent pad assembly 11 includes a pad 311 which has a rapid fluid strike-through lattice structure disposed inside an envelope 309. The cover stock or envelope 309 comprises a soft, nonwoven fabric made of polystyrene, for example. The envelope is folded over at the edges and ends wherein the polyester fabric surrounds or encloses the remainder of the pad. The edge seams 333, as well as the end seams 316, can be formed by a hot-melting adhesive, thermal welding or any other suitable process. The ends of the envelope 309 can be closed at both ends by weld seams produced by known welding techniques such as ultrasonics, thermowelding or the like.

When the weld seams are produced, the absorbent pad 311 is completely enclosed but is not necessarily adhered to the envelope 309.

The absorbent pad 311 is multi-layered and comprises, in a preferred embodiment, super absorbent polyacrylate cellulose, cellulose powder or the like within layers of superabsorbent laminate for high fluid retention. The pad 311 can be fluted, with a plurality of holes punched therein or therethrough. The pad may also include hinged components 325 formed from the materials produced as a result of the punched holes. The holes and/or hinged components (both of which are optional) as well as the fluting function to help distribute fluid rapidly and evenly throughout.

For example, the absorbent pad 311 comprises a cover 308, comprising in the preferred embodiment, a 2-ply tissue formed of layers 308A and 308B. This cover enclosed a cellulose layer 307. This is followed by a 2-ply tissue layer 305 comprising layers 305A and 305B. Layers of polyacrylate powder are disposed on, or incorporated into, the cellulose layers 303 and 307.

Thus, because of the absorbent effect of the absorbent cellulose layers, wound secretions are taken up through the polypropylene fabric of envelope 309 into the absorbent pad 11. The hydrophobic preparation given to the fleece of cellulose layer 303 prevents wound secretion being discharged upwards and the hydrophobic properties of the polypropylene fabric of layer 307 prevent discharge in the downward direction.

It may be noted here that the phrase "surgical dressing" as used herein is not limited to the use of the dressing only to surgical wounds or to surgical procedures alone, but it intended to be a term of art which designates any material which is applied to cover any bodily lesion, opening or wound and the like.

Thus, there is shown and described a unique design and concept of absorbent surgical dressing and process for manufacturing same. While this description is directed to a particular embodiment, it is understood that those skilled in the art may conceive modifications and/or variations to the specific embodiments shown and described herein. Any such modifications or variations which fall within the purview of this description are intended to be included therein as well. It is understood that the description herein is intended to be illustrative only and is not intended to be limitative. Rather, the scope of the invention described herein is limited only by the claims appended hereto.

What is claimed is:

1. An absorbent surgical dressing comprising, a thin, flaccid support tape having a medical grade adhesive surface, said support tape comprises a fluid impervious membrane fabricated of breathable material, a preformed release liner disposed on a portion of said tape at the adhesive surface thereof, a highly absorbent pad assembly adhered to the adhesive surface of said tape which is not covered by said release liner whereby said preformed release liner surrounds said pad assembly on said support tape, said pad assembly includes an absorbent pad and an external envelope which surrounds said absorbent pad and is permeable to fluids, said absorbent pad includes holes punched therein for even distribution of any fluid absorbed in said absorbent pad, and a removable backer sheet for selectively supporting said support tape until said backer sheet is removed and the dressing is applied to a surface.

2. The dressing recited in claim 1 wherein, said tape is transparent.

3. The dressing recited in claim 1 wherein, said tape is translucent.

4. The dressing recited in claim 1 wherein, said absorbent pad includes multiple layers of absorbent material within said external envelope.

5. The dressing recited in claim 4 wherein, said absorbent material comprises at least one layer of cellulose material.

6. The dressing recited in claim 1 wherein, said external envelope is fabricated of a non-woven polyester material.

7. The dressing recited in claim 1 wherein, said release liner is fabricated of at least one of the group of materials composed of paper, gauze and plastic.

8. The dressing recited in claim 1 wherein, said release liner includes at least one slit therein.

9. The dressing recited in claim 1 wherein, said pad assembly comprises a cellulosic material.

10. The dressing recited in claim 1 wherein, said envelope comprises a non-woven polyester material.

11. The dressing recited in claim 1 wherein, said support tape comprises a polyurethane material.

12. The dressing recited in claim 1 wherein, said removable backer sheet includes at least one slit therein.

13. The dressing recited in claim 1 wherein, said absorbent pad is free to move within said external envelope.

14. The dressing recited in claim 8, wherein, said slit in said release liner facilitates the removal of said release liner from said support tape.

15. The dressing recited in claim 12 wherein, said slit in said backer sheet facilitates removal of said backer sheet from said support tape.

* * * * *